United States Patent [19]
Biedermann

[11] Patent Number: 5,376,134
[45] Date of Patent: Dec. 27, 1994

[54] ADJUSTABLE ORTHESIS JOINT

[75] Inventor: Lutz Biedermann, Schwenningen, Germany

[73] Assignee: Biedermann Motech GmbH, Schwenningen, Germany

[21] Appl. No.: 173,273

[22] Filed: Dec. 23, 1993

Related U.S. Application Data

[63] Continuation of Ser. No. 972,967, Nov. 6, 1992, abandoned.

[30] Foreign Application Priority Data

Nov. 11, 1991 [DE] Germany .................. 4137057

[51] Int. Cl.$^5$ .................. A61F 2/64; A61F 2/68; A61F 2/62
[52] U.S. Cl. .................. 623/39; 623/42; 623/46; 602/16; 602/26
[58] Field of Search .................. 623/39, 42, 46; 602/16, 602/26

[56] References Cited

U.S. PATENT DOCUMENTS

| | | | |
|---|---|---|---|
| 4,145,766 | 3/1979 | May | 623/39 |
| 4,215,442 | 8/1980 | Blatchford et al. | 623/39 |
| 4,310,932 | 1/1982 | Nader et al. | 623/39 |
| 4,353,361 | 11/1982 | Foster . | |
| 4,489,718 | 12/1984 | Martin . | |
| 4,493,316 | 1/1985 | Reed et al. . | |
| 4,619,660 | 10/1986 | Christiansen et al. | 623/46 |
| 4,685,927 | 8/1987 | Haupt | 623/46 |
| 4,854,308 | 8/1989 | Drillio . | |
| 4,886,054 | 12/1989 | Castillo et al. . | |
| 4,911,709 | 3/1990 | Marlow et al. | 623/39 |
| 4,928,676 | 5/1990 | Pansiera | 128/80 F |
| 5,022,391 | 6/1991 | Weidenburner | 602/26 X |
| 5,060,640 | 11/1991 | Rasmusson . | |
| 5,062,858 | 11/1991 | Broeck et al. | 623/39 X |

FOREIGN PATENT DOCUMENTS

| | | |
|---|---|---|
| 0382976A1 | 12/1989 | European Pat. Off. . |
| 0454186A2 | 10/1991 | European Pat. Off. . |
| 2215394A | 9/1989 | United Kingdom . |

OTHER PUBLICATIONS

European Search Report with Annex.

Primary Examiner—Randall L. Green
Assistant Examiner—Dinh X. Nguyen
Attorney, Agent, or Firm—Donald Brown

[57] ABSTRACT

An orthesis joint comprises a first support plate, a thigh attachment part hingedly connected to the first support plate through a first bearing bush, a lower leg attachment part hingedly connected to the first support plate through a second bearing bush, a connecting member hingedly connected with both attachment parts through a third and fourth bearing bush, respectively, and means for limiting the movement of the joint. It is desired to achieve a simple design for the limit means. To this end one of the attachment parts comes into engagement with the connecting member by a first and a second stop, respectively, and at least one of the stops is adjustable.

6 Claims, 3 Drawing Sheets

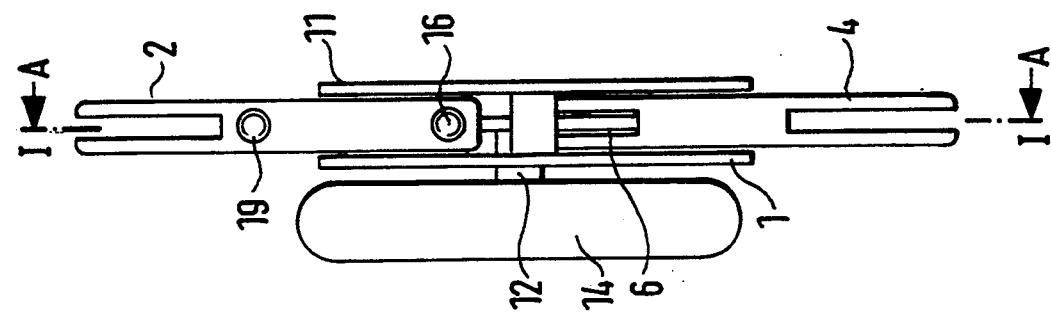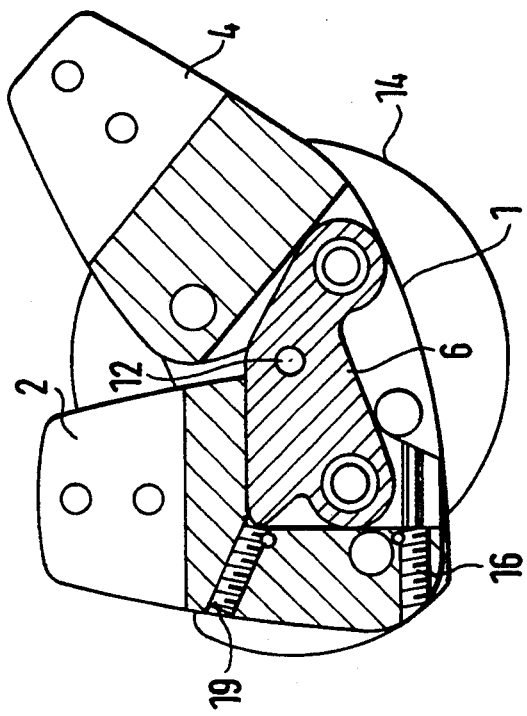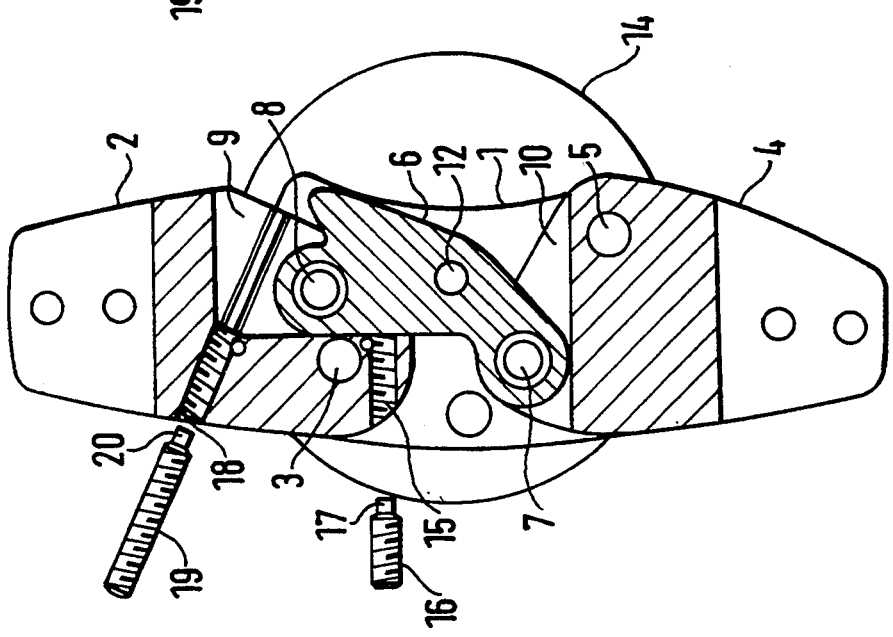

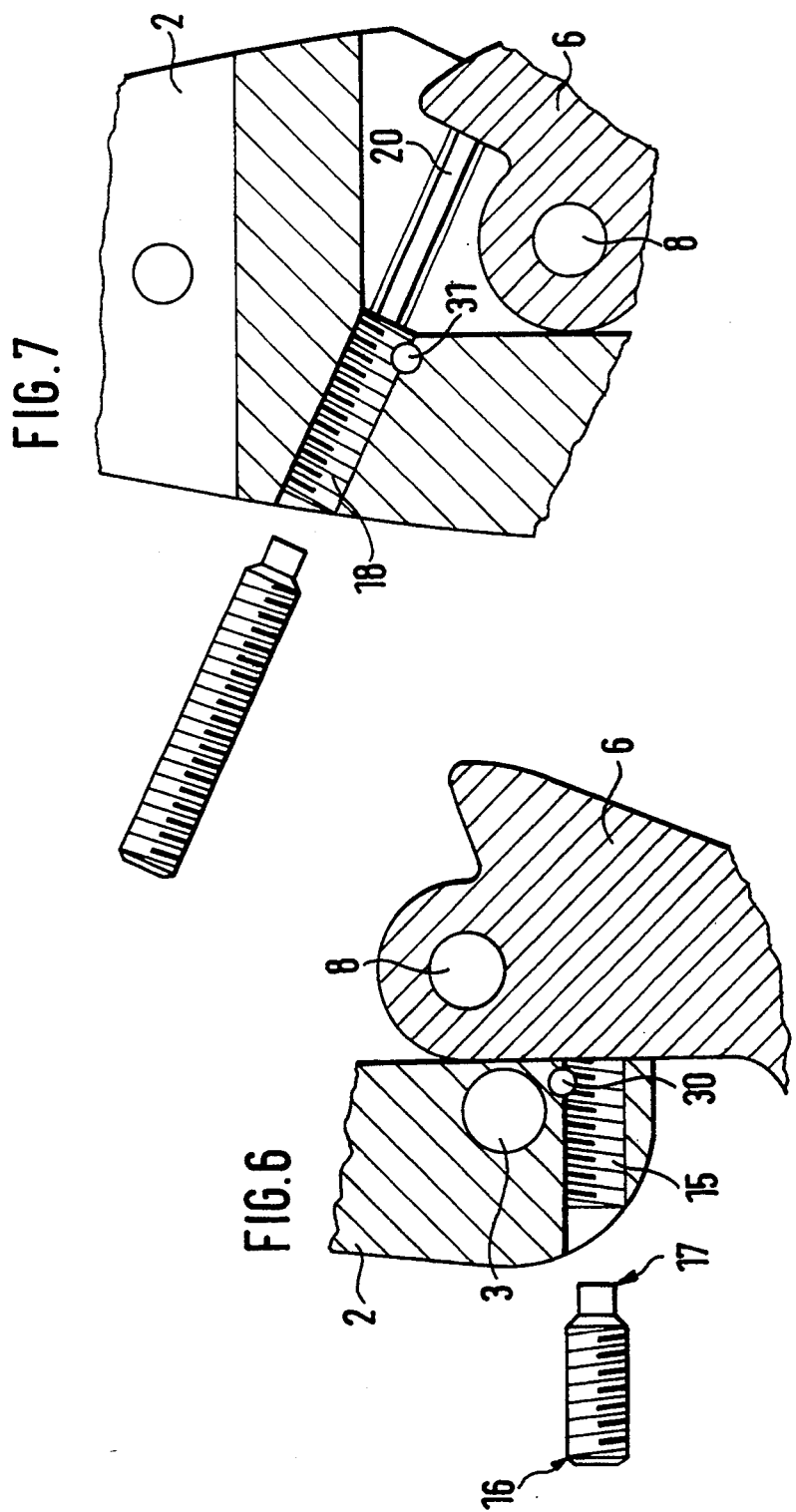

ADJUSTABLE ORTHESIS JOINT

This is a continuation of copending application(s) Ser. No. 07/972,967 filed on Nov. 6, 1992 abn for FWC.

BACKGROUND OF THE INVENTION

The invention relates to an orthesis joint which is in particular used as a knee joint for leg ortheses.

Such an orthesis joint is known from U.S. Pat. No. 4,886,054. A slotted guide housing is mounted on the support plate for limiting the stretching movement and the flexing movement, respectively, of the joint. A lever having a ball at the free end thereof is connected with the upper attachment part. The lever is inserted into the housing such that the ball moves therein and the lever projects outwards through the slot. The length of the guide within the housing is defined by two screws which are provided at respective opposite ends thereof and form respective stops. This design of the stop limits is extraordinarily complicated and expensive. Further, it has the drawback that there are partly obliquely acting forces which may cause malfunctions. Moreover, the fact that the ball directly strikes the respective stops results in uncomfortable wearing characteristics at the respective stop.

OBJECTS OF THE INVENTION

It is an object of the invention to provide an improved orthesis joint in which the above-mentioned drawbacks are avoided. It is a further object to provide an orthesis joint having a simplified design of the adjustable means for defining the movement of the joint. It is a still further object of the invention to improve the wearing characteristics of the orthesis.

SUMMARY OF THE INVENTION

In order to achieve the above-mentioned objects, the invention provides an orthesis joint comprising a first support plate, a thigh attachment part which is hingedly connected to said first support plate through a first bearing bush, a lower leg attachment part which is hingedly connected to said first support plate through a second bearing bush, a connecting member which is hingedly connected to both said attachment parts to a third and fourth bearing bush, respectively, and at least one first adjustable stop defining an engagement of said connecting member with one of said attachment parts.

According to a further embodiment of the invention a pressure cushion is provided which is arranged so as to avoid a movement thereof in relation to the knee when moving the knee joint. This also leads to a substantial improvement of the wearing comfort.

BRIEF DESCRIPTION OF THE DRAWINGS

Further features and advantages of the invention result from the description of an embodiment with reference to the figures. In the figures:

FIG. 1 is a sectional view along line A—A in FIG. 3 with the orthesis joint being in stretched end position;

FIG. 2 is a corresponding representation of the joint in flexed end position;

FIG. 3 is a front view of the orthesis joint;

FIG. 6 shows a detail of FIG. 1 in enlarged representation; and

FIG. 7 shows a further detail of FIG. 1 in enlarged representation.

DESCRIPTION OF A PREFERRED EMBODIMENT

Figure 4:
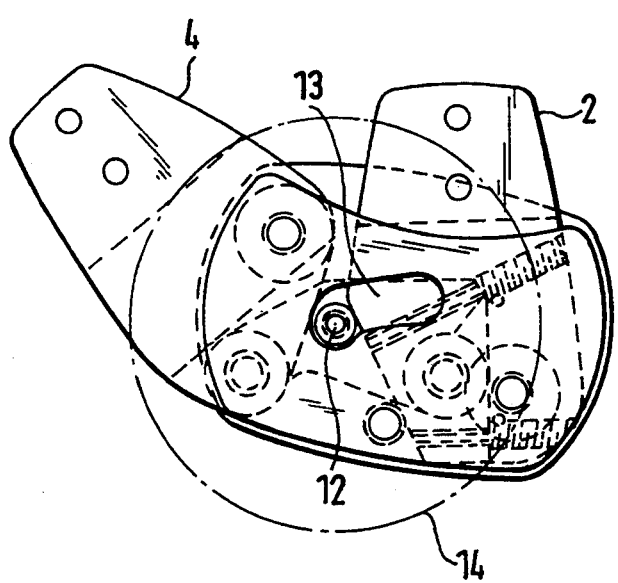
FIG. 4 is a back view of the orthesis joint shown in FIG. 2 with pressure cushion indicated in dotted lines.

The orthesis joint comprises a first support plate (1). A thigh attachment part (2) is hingedly connected thereto at a bearing bush (3) extending perpendicular to the plane of the support plate. Further, a lower leg attachment part (4) is provided which is hingedly connected with the support plate (1) at a second bearing bush (5) extending perpendicular to the plane of the support plate. A connecting member (6) is provided between both attachment parts. This connecting member has one end thereof hingedly connected to the lower leg attachment part (4) at a third bearing bush (7) and the other end thereof hingedly connected to the thigh attachment part (2) at a fourth bearing bush (8).

The connection between the connecting member and the attachment parts is made such that slotted recesses (9, 10) extending parallel to the support plate are provided at the facing ends of the attachment parts. The connecting member is movably guided within these recesses. As may be best seen from FIG. 3, a second support plate (11) is provided which is a mirror image of the first support plate. The ends of the respective bearing bushes which are facing away from the first support plate are supported in the second support plate. The attachment parts are freely movable between both support plates.

Figure 5:
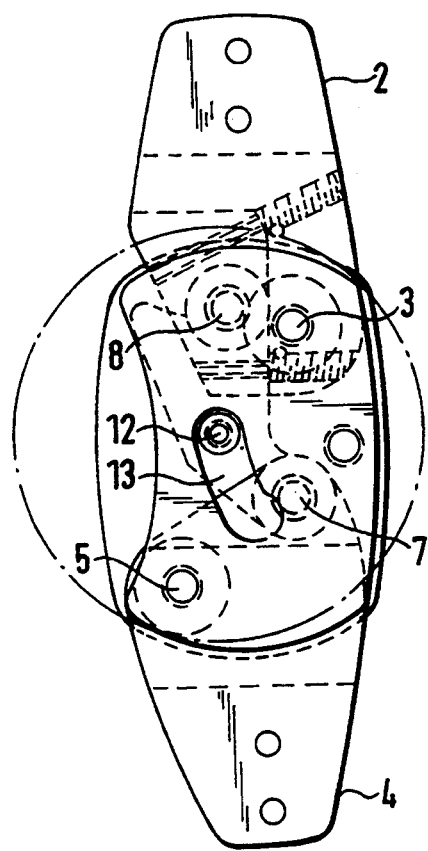
FIG. 5 is a back view of the orthesis joint shown in FIG. 1 with the pressure cushion indicated in dotted lines.

The position of the first to fourth bearing bushes is selected in per se known manner such that a first straight line connecting the first and second bearing bush intersects the second straight line connecting the third and fourth bearing bushes with an angle such that a motion having a substantially circular portion and a following substantially spiral portion results from the two joints formed by the first and second bearing bushes when moving the attachment parts or the orthesis connected thereto, respectively. The connecting member (6) has a threaded bush (12). In FIGS. 1 and 2 the rear side of the rivet connecting the threaded bush with the connecting member can be seen, whereas the threaded bush itself is shown in FIGS. 3 to 5. The first support plate (1) comprises a hole (13) having a size such that the threaded bush (12) can freely move through the hole when moving the orthesis joint. A pressure cushion (14) is rigidly connected to the connecting member (6) through the threaded bush (12) by means of a suitable screw. As may be best seen in FIG. 1, the threaded bush (12) is arranged on a line which extends perpendicular to the longitudinal axis of the stretched orthesis joint and which is about equally spaced from the first bearing bush (3) and from the second bearing bush (5). In a side view it is positioned on a straight line which extends parallel to the longitudinal axis of the stretched orthesis joint and which is about equally spaced from the first and second bearing bush. The rigid connection of the pressure cushion with the connecting member (6) achieves that the pressure cushion no longer moves up and down or back and forth, respectively, when moving the orthesis joint.

As may be best seen the FIGS. 1 and 2, a first threaded bore (15) is provided in the center plane of the thigh attachment part (2) and extends parallel to the support plate. A threaded sleeve (16) comprising a stop

(17) which is prestressed by an interior spring is screwed into the bore (15). The screw is adjusted, dependent on the needs of the patient, such that the stretched end position shown in FIG. 1 is defined by the stop. Further, a second threaded bore (18) is provided and as corresponding threaded sleeve (19) having a stop (20) prestressed by an interior spring is screwed into the threaded bore (18). As may in particular be seen from FIG. 2, the flexed end position of the orthesis joint is defined by the screw-in location of the threaded sleeve with the stop. The spring's prestress or an elastic prestress produced by means of a rubber, if desired, respectively, prevents a hard collision of the orthesis parts when wearing the same, so that the wearing comfort is considerably improved.

FIGS. 6 and 7 show detailed enlarged representations of the buffered stops. FIG. 6 shows the abutment in an unscrewed state, FIG. 7 shows a stop in screwed-in state and a further stop in an unscrewed state for demonstration purposes. As may in particular be seen from both figures, a respective asymmetrically supported locking pin (30) and (31), respectively, is provided such that in the above described resilient abutment an unintentional change of position of the inserted screw is prevented by turning the locking pin into the locking position.

In the above described embodiment the two threaded sleeves forming the stops are arranged in the thigh attachment part. Basically it is also possible to modify the lower leg attachment part and to provide the stops within the lower leg attachment part. It is further possible to arrange one of the stops in one of the attachment parts and the other stop in the other attachment part.

Although the invention has been described with reference to a specific example embodiment, it is to be understood that it is intended to cover all modifications and equivalents within the scope of the appended claims.

What is claimed is:

1. An orthesis joint comprising a first support plate (1) having a side wall, a thigh attachment part (2) which is hingedly connected to said first support plate (1) through a first bearing bush (3), a lower leg attachment part (4) which is hingedly connected to said first support plate (1) through a second bearing bush (5), a connecting member (6) which is hingedly connected to both said attachment parts (2,4) through a third (7) and fourth (8), respectively, bearing bush, at least one first adjustable stop defining an engagement of said connecting member with one of said attachment parts, and said at least one first stop is elastic, a fifth bush (12) coupled to said connecting member side wall and extending perpendicular thereto and moveable therewith, said support plate (1) defining an opening (13) in which said fifth bush (12) is moveable therein when moving the orthesis joint, said fifth bush (12) extending beyond said opening (13) in said support plate (1) and a cushion (14) rigidly connected to said fifth bush portion (12) which extends beyond said opening (13) in said support plate (1).

2. An orthesis joint comprising a first support plate (1), a thigh attachment part (2) which is hingedly connected to said first support plate (1) through a first bearing bush (3), a lower leg attachment part (4) which is hingeldy connected to said first support plate (1) through a second bearing bush (5), a connecting member (6) which is hingedly connected to both said attachment parts (2,4) through a third (7) and fourth (8), respectively, bearing bush and at least one of said attachment parts having a slot (9) into which the connecting member (6) moves back and forth, said attachment member (2) with said slot (9) also containing a bore in which there is positioned a spring loaded stop means which extends into said slot (9) for engagement with said connecting member (6).

3. The orthesis joint of claims 1 or 2 wherein said at least one stop is formed as a threaded sleeve (16), which is supported in threaded bore (15), as said at least one stop has a spring-biased stop head (17).

4. The orthesis joint of claim 1, said pressure cushion (14) having a center which is positioned essentially on a line extending perpendicular to a longitudinal direction of the orthesis joint, being in a stretched position which corresponds to a position of the orthesis joint mounted on a stretched leg, and this line being about equally spaced from said first and second bearing bushes.

5. The orthesis joint of claim 4, comprising a slot in at least one of said attachment parts at a region thereof facing the other of said attachment parts for guiding said connecting member therein.

6. The orthesis joint of claim 2, comprising a second support plate disposed on side of said attachment parts opposite to said first support plate, one of said support plates having a hole and a connecting means connecting said connecting member with said pressure cushion extending through said hole.

* * * * *